United States Patent

Ayoub et al.

[11] Patent Number: 5,518,700
[45] Date of Patent: May 21, 1996

[54] CYCLONIC REACTOR

[75] Inventors: Paul M. Ayoub; Jean-Charles Ginestra, both of Houston, Tex.

[73] Assignee: Shell Oil Company, Houston, Tex.

[21] Appl. No.: 264,825

[22] Filed: Jun. 25, 1994

[51] Int. Cl.$^6$ .............................. B01F 5/04; B01D 47/06
[52] U.S. Cl. ........................... 422/225; 422/231; 422/257; 261/117; 366/173.200
[58] Field of Search .................................... 422/194, 224, 422/225, 231, 257, 278; 570/234; 261/31, 32, 79.1, 83, 84, 88, 89, 117, 118; 366/167, 173

[56] References Cited

U.S. PATENT DOCUMENTS

| | | | |
|---|---|---|---|
| 2,759,800 | 8/1956 | Hill | 422/257 |
| 2,763,699 | 9/1956 | van Dijk et al. | 570/234 |
| 3,054,831 | 9/1962 | Samples et al. | 570/234 |
| 3,488,159 | 1/1970 | Moon et al. | 422/257 |
| 3,595,297 | 7/1971 | Berg | 422/257 X |
| 3,692,763 | 9/1972 | Van Saane et al. | 526/88 |
| 3,914,110 | 10/1975 | Anderson | 422/194 X |
| 4,590,044 | 5/1986 | Mos et al. | 422/191 |
| 4,870,220 | 9/1989 | Jabrik et al. | 570/234 |
| 5,037,619 | 8/1991 | Alagy et al. | 422/191 |
| 5,156,821 | 10/1992 | Murayama | 422/191 |
| 5,367,105 | 11/1994 | Miyazaki et al. | 570/234 |
| 5,368,825 | 11/1994 | Calcote et al. | 422/198 |

FOREIGN PATENT DOCUMENTS 742356  11/1969  Belgium.
32087   3/1968   Japan.

OTHER PUBLICATIONS

"High temperature chlorination of propylene in a cyclonic reactor," *International Chemical Engineering*, vol. 2, No. 1, published Jan. 1962.

*Primary Examiner*—Robert J. Warden
*Assistant Examiner*—Christopher Y. Kim
*Attorney, Agent, or Firm*—Todd F. Volyn

[57] ABSTRACT

A reactor having one or more reactant inlets to which spargers are affixed and one or more reactant inlets each having an injection jet is presented. Reactants are introduced into the reactor through the spargers and jets under conditions in which a three dimensional cyclonic character is created in a well mixed reaction zone. This, together with the energy with which the reactants are introduced into the reaction zone, facilitates both macromixing and micromixing phenomena. The reactor is particularly useful for reacting chlorine and propylene to obtain allyl chloride.

15 Claims, 2 Drawing Sheets

CYCLONIC REACTOR

FIELD OF THE INVENTION

This invention relates to chemical reactors.

BACKGROUND OF THE INVENTION

Ensuring that reacting species achieve optimal physical contact can be among the most difficult challenges in chemical reactor design. If done improperly, numerous undesired byproducts and an abundance of unreacted reactants can seriously erode the economics of the system. The volume of the reaction zone, the reactor type (i.e., batch, plug flow, stirred tank, or combinations thereof), thermal effects, reaction mechanism, reactant and product diffusion, pressure effects, and other factors must all be considered in selecting or fabricating a reactor best suited for use in a given reaction.

Of course, the nature of the reaction that is to occur in the reactor has much to do with the selection of the reactor. If a reaction mechanism only involves the bimolecular collision of small molecules, all that is desired is a contact between the two species at an energy state that provides a good chance for bonding to occur. Providing reactants with a particular residence time in a reactor may be necessary to increase the percentage of atomic or molecular collisions. However, if one or more of the reactants is capable of bonding at numerous sites greater residence time can also result in the production of numerous byproducts. This can be the case, for example, where diolefins are used as reactants. Thus, there is a balance that is sought between attaining complete reaction and overreacting or incorrectly reacting the reactants. The kinetics of reactions that involve more than simple bimolecular collisions are more complex and add to the factors one must consider.

Backmixing is another phenomenon which can contribute to further reaction of the reactor products. Backmixing is the mixing of a molecule or intermediate which has been present in the reactor for a given length of time with a molecule or intermediate which has been present in the reactor for a lesser period of time. The amount of backmixing that occurs is related to reactor geometry and type, fluid dynamics and other factors involved in reactor operations as noted above.

In commercial operations, the economic impact of a particular design is critical. These factors include the theoretical yield, side reactions, and process flow. Any process in competition with the desired reaction will result in a loss of value or an increase in costs due to recirculation of unreacted species and separation and treatment of byproduct. Other costs such as the cost of increased maintenance of equipment due to problems such as coke fouling can also appear.

It is well known that designing commercial chemical reactors is not amenable to a purely theoretical treatment. Typically, one begins the process by considering the reaction type (eg, reaction kinetics), catalytic requirements, phases involved, temperature and pressure effects on the reaction, production requirements, heat and mass transfer effects on the reaction, and secondary factors such as whether corrosion of the reaction vessel is likely. One then typically selects an ideal reactor that appears most applicable given these factors. For example, where the reaction mechanism suggests that back mixing would be particularly harmful, one may start with an analysis of an ideal plug flow reactor. Where back mixing is desired, a stirred tank may be selected.

Once an ideal reactor is selected, one then typically determines correction factors to account for deviations between the ideal and real behavior of the reaction. This is necessarily an experimental process. When the correction factors are determined, the reactor designer can then determine parameters such as reactor size and shape, whether the design (type) should be hybridized, and controls for parameters such as temperature and pressure. At this point, one may have the information that appears necessary to design an experimental reactor. Experimental reactors are then fabricated and tested.

The jump from the design of an experimental reactor to the design and production of a commercial or scaled-up reactor is necessarily a difficult one. For example, changes in reactor volume alone can greatly change operational parameters of what was previously thought to be a well understood system. Fluid dynamics, the nature of the reaction sites, reaction rates, and mass and heat transport considerations further complicate the problem.

The extent to which reaction conditions can be controlled is dictated, in large part, by the type of apparatus employed to conduct the reaction. Numerous reactors have been designed to solve particular problems. For example, U.S. Pat. No. 2,763,699 describes an apparatus for creating homogeneous turbulence of vapor phase reactants in curved reactors through the tangential positioning of injection nozzles about the inner surface of the vessel. It was found that use of the reactor therein described decreased the formation of carbon deposits that accompanies the production of allyl chloride from propylene and chlorine. Tangential injection essentially resulted in a two dimensional flow of reactants that traced the inner surface of the reactor.

U.S. Pat. No. 4,590,044 is an example of a reactor designed to ameliorate the effect of temperature variability in endothermic and exothermic reactions. This is done through the use of a number of baffles or reaction zones within the reactor.

Japanese Patent J73032087-B describes a reactor constructed specifically for the gas phase chlorination of hydrocarbons. The vessel used to mix the reactants is oblong having two opposing parallel flat surfaces and two opposing curved surfaces (when viewed in cross section). Jets are used to introduce the preheated reactant into the vessel tangentially and from opposing sides so that a swirl develops. This is said to allow increased heats of reaction and better mixing over previous reactor design. The reaction zone, or area in which the reaction occurred within the reactor, is essentially the entire inside volume of the reactor. While the tangential introduction of reactants creates a swirling effect, this effect is also predominantly a two dimensional effect. That is, swirling occurs essentially in one plane and traces the inner surface of the reactor. Further, since the reaction zone comprises essentially the entire inner volume of the reactor, there can be only one reaction zone.

Belgian Patent 742,356 describes a process for synthesizing allyl chloride by gas phase substitutive chlorination of propylene. The reactors used in this process incorporate a number of reaction zones. However, the process was designed specifically to avoid what the inventor viewed as the complex engineering necessary in reactors that incorporate a swirling or cycloning effect on reactants. Thus, here too, the reaction zone in such a system essentially comprises the entire inside volume of the reactor. The examples cited in the patent all employ a series of tubular reactors to accommodate this methodology.

Dykyj et al. describe a cyclonic reactor in *High Temperature Chlorination of Propylene in a Cyclonic Reactor, Inter-*

*national Chemical Engineering* (Czecholoslovakia January, 1962). This design incorporates injection jets which introduce reactants tangentially to the inner surface of a cylindrical vessel. The jets are placed in opposition relative to the central axis of the reactor. However, they are offset so that they are not in direct opposition to each other. This causes the reactants to travel concentric to the inside surface of the reaction vessel so that a cyclonic effect is achieved. The authors assumed that no mixing would occur in the center part of the reactor and filled that portion of the reactor with a metallic core. Thus, the reaction zone in this arrangement appears as a cylinder with a hollow core (i.e. doughnut shaped). The movement of the reactants occurs in essentially two dimensions found in a circular plane with a hole in its center.

When a reactant is directed against a surface of the reactor, such as in the case of tangential injection, additional considerations arise. For example, if the reactant is a corrosive material such as chlorine, the reactor will frequently require special construction. One such method is to provide the interior surface of the reactor with a nickel coating. Such measures can dramatically increase the cost of the reactor.

Turbulent, swirling, and cyclonic flow reactors increase the likelihood of a collision between reacting species beyond what would be found if reactants were merely injected into a reactor without inducing motion on the reactants. However, prior art reactors generally induce motion in a single plane. At best, such reactors exhibit cocurrent mixing. This is predominantly a macromixing effect which folds layers or provides an overall flow to the stream of reactants. Some molecular collisions occur between the planes that are flowing but they are relatively few in number and occur by virtue of happenstance rather than design. The addition of heat and longer residence times can be used to induce such collisions but yield and selectivity losses generally accompany such measures as outlined above. In many instances adiabatic reaction design is preferred so adding heat to achieve greater frequency of collisions is not possible.

These problems are particularly acute where a number of possible reaction mechanisms may occur between reactants. The reaction between unsaturated hydrocarbons and halogens provides a good example of such a case. Either substitution reactions, addition reactions, or both may occur. Substitution reactions are preferred in the production of allyl chloride from propylene and chlorine. Higher temperatures are often necessary to create conditions more favorable to this substitution than addition reactions. Unfortunately, temperatures that are too high can result in the undue formation of coke and other undesirable substances and effects. Improperly increasing residence time might also create undesirable byproducts and reduce reaction selectivity.

Because the substitution reaction is preferred in the commercial preparation of allyl chloride as noted above, prior art reactors use increased temperatures to avoid the production of the by-product 1,2 dichloropropane (DCPo). These high temperature reactions are typically accompanied by the production of coke. The reaction may actually exhibit varying kinetic characteristics within one reactor because of the formation of hotspots. Numerous other reactions involving, for example, the selective chloro-substitution of ethylene, butylene, pentenes, hexenes, octenes, cyclohexene, acetylene, etc also experience such problems.

The art of reactor design could greatly benefit from the introduction of a reactor which would improve molecular contact, allow greater selectivity, and decrease reaction time/residence time substantially without the formation of coke and byproducts. This is particularly true in the case of the commercial preparation of allyl chloride from propylene and chlorine.

SUMMARY OF THE INVENTION

It is an object of this invention to provide a chemical reactor for reacting gaseous or vapor phase reactants to provide high yields and selectivities for reactions conducted therein.

It is a further object of this invention to provide a chemical reactor with improved mixing characteristics.

It is yet a further object of this invention to provide a multistage reactor and method for producing allyl chloride.

It is yet a further object of this invention to provide a reactor with a reaction zone having substantial three dimensional flow character.

In accordance with these and other objects of this invention, a reactor is provided comprising:

a reaction vessel;

a reaction zone introduction means having at least two ends, said introduction means being in communication with a source of reactant at one of said ends and the interior of said reaction vessel at said other end;

at least one injection jet in communication with a source of reactant, said injection jet housed within said reaction vessel; at least one reactant of a chemical reaction being introduced into said reactor through said reaction zone introduction means, at least one reactant being introduced into said reactor through said injection jet, said injection jet positioned so that introduction of said reactants imparts a substantially three dimensional flow of said reactants;

a well mixed reaction zone within said reaction vessel wherein said reactants are mixed;

and an outlet having two ends, one end being in communication with the interior of the reaction vessel and one end being in communication with the exterior of the reaction vessel.

In one aspect of the invention, spargers comprise the reaction zone introduction means. Preferably, at least two sets of such spargers are disposed in opposition to each other and cyclonic three dimensional flow character is induced in the reaction zone.

The reactor of this invention can also have a staged construction so that the chemical reaction is initiated in a well mixed reaction zone substantially comprising the area between the spargers and then attains a desirable residence time in a plug flow zone within the reactor before product is withdrawn.

The reactors and methods herein presented can be applied to the production of allyl chloride from propylene and chlorine such that the production of bothersome byproducts are greatly reduced over what was found in the prior art.

DETAILED DESCRIPTION OF THE INVENTION

Reaction selectivities, time of reaction, and other parameters of chemical reactions have been enhanced by providing a chemical reactor with one or more novel reaction zones. The reaction zones are shaped and charged so that the energy required of the reaction is rapidly attained. As will be seen throughout this description, these new methods of defining reaction zones can be structured from the juxtaposition of jets; spargers, nozzles and other vehicles for injecting reactants into a chemical reactor.

Definitions

As used throughout this specification, "reaction zone" means an area in which a reaction or a discrete phase of a reaction is substantially conducted. A chemical reactor can have more than one reaction zone.

"Well mixed reaction zone" means a reaction zone in which reactants are mixed to form a mixture which is more homogeneous than not. A CSTR (continuously stirred tank reactor) comprises an ideal well mixed reaction zone.

"Three dimensional flow" means the movement of molecules in such a manner that collisions between such molecules can occur outside of the plane in which such molecules are initially found as well as inside the plane in which they are initially found. Substantial three dimensional flow is the movement of molecules characterized by three dimensional flow but also comprising some two dimensional flow. For example, a reaction zone in which reactants flow in three dimensions except in planes at the fringes of the zone exhibits substantial three dimensional flow.

"Three dimensional" with respect to mixing refers to a flow of molecules resulting in a complete or homogeneous mixture in all directions. By way of example, a CSTR exhibits three dimensional mixing while a Plug Flow Reactor only exhibits complete mixing radially.

"Sparge" means injecting or introducing a compressed or pressurized fluid through a sparger.

A "sparger" is a vessel having a perforation, with or without a fixture thereto, used to inject or introduce a compressed or pressurized fluid into an area in a gaseous or atomized state.

A "transverse axis" is an axis along the longest dimension of an object.

A "transverse plane" is a plane having its length defined by a transverse axis.

A "central axis" is an axis running through the center of an object along it longest dimension. The central axis of a cylinder runs through the center of the circle comprising its cross section and extends through the length of the cylinder.

A "longitudinal plane" is a plane drawn running through an object along its longest dimension.

Figure 1:
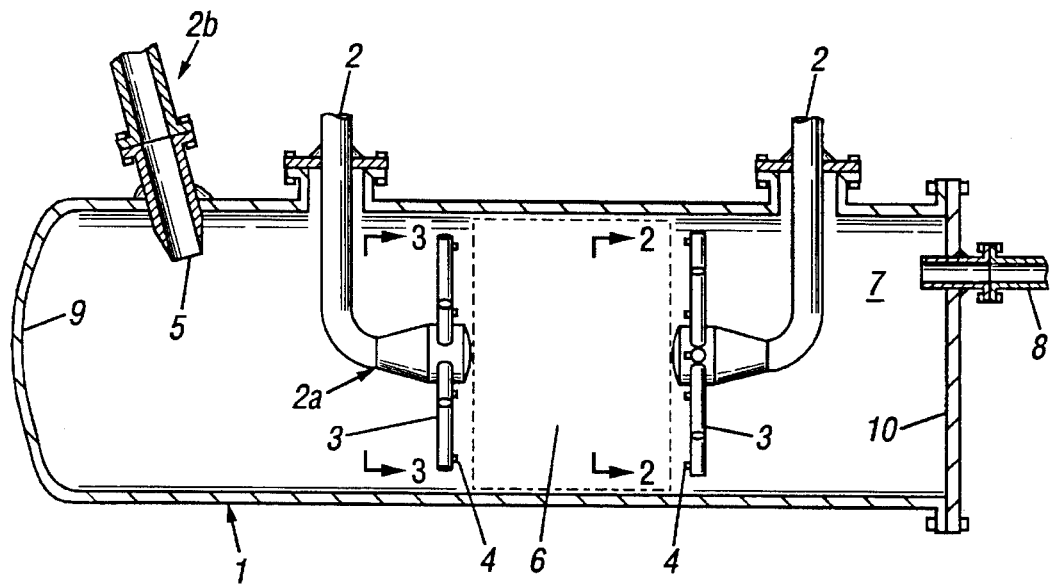
FIG. 1 is a side cutaway view of an embodiment of the reactor of the instant invention.

Turning to the drawings, FIG. 1 is a cutaway view of a preferred reactor of the instant invention. The reaction vessel 1 is shown as an oblong cylinder but overall body shape is not critical to this invention. One or more reactants are introduced to the interior of the reaction vessel 1 by means of reactant inlets 2. Reactant inlets 2 are pipes, conduit, tubing or any of the means typically used for introducing gaseous reactants into a reaction vessel. Two opposing reactor inlets are preferred. It will be understood that when reference is made throughout this specification to a first or other reactant that no particular order of injecting or reacting such reactants is implied or suggested.

A sparger 3 is affixed to the end of the reactant inlet 2 on the interior of the reactor. This combination of sparger and reactant inlet comprise an example of a reaction zone introduction means but numerous other means can be used in the place of this particular means. Such means must be capable of transporting reactant from a source to an area inside the reaction vessel such that reactant is placed in the reaction zone. The spargers 3 are fashioned from pipes or other essentially hollow vessels for distributing reactants to nozzles 4. Ultimately, reactants are expelled into the interior of the reactor through these nozzles 4. The spargers 3 as shown are essentially perpendicular or normal to the central axis of the inlet ends 2a although this is not an essential aspect of positioning the sparger in every embodiment of the instant invention. Rather, placement and spacing of the spargers 3 is determined by the character of reactant flow and mixing which is ultimately desired. This will be discussed more fully below.

Figure 2:
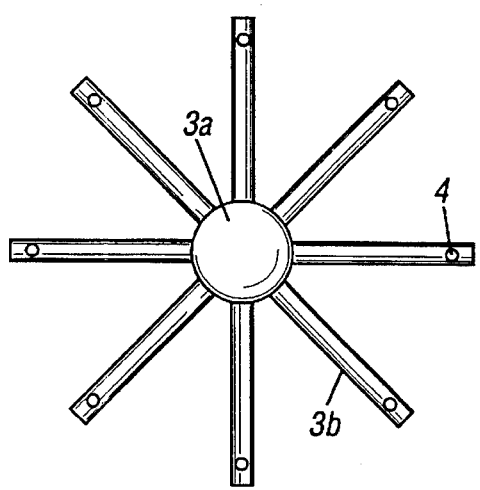
FIG. 2 is a front view of a sparger used in the reactor of the instant invention.

In the most preferred embodiment of the instant invention, spargers 3 are positioned so that the nozzles affixed to them are in substantial opposition. That is, the nozzles 4 face each other and are parallel to the central axis of the reactors but can be twisted, moved away from or moved towards the central axis of the reactor by up to 15°. FIG. 2 illustrates the structure of the spargers 3 in more detail. There it is shown that sparger arms 3b radiate outward (away from) sparger hub 3a. Nozzles 4 are positioned along the sparger arms 3b.

Figure 3:
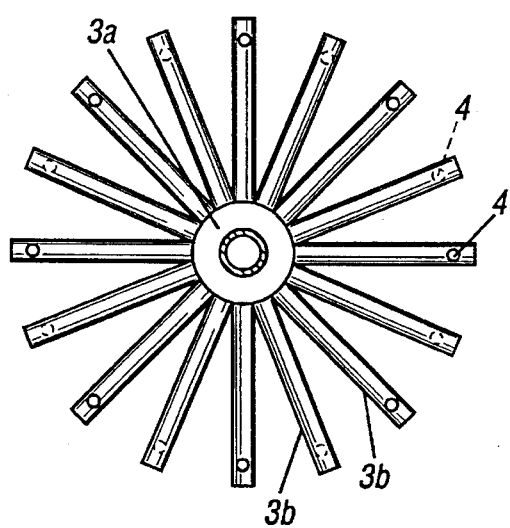
FIG. 3 is a front view of a sparger used in the reactor of the instant invention as such a sparger could be juxtaposed to the sparger of FIG. 2.

In this embodiment, spargers 3 are positioned so that the sparger arms 4 of one sparger substantially bisect the distance between the sparger arms of another opposing (ie, facing) sparger. That is, one sparger arm is positioned to point anywhere in the area between two opposing spargers. The relative angular positioning of such an opposing sparger is shown in FIG. 3. Such an arrangement contributes to the desirable flow and mixing characteristics of the reactants. Spargers may also be made in a circular or oblong shape with numerous nozzles or holes cut therein. Such a sparger can, for example, be fashioned to take on the appearance of a shower head. It is preferred that nozzles not be placed along the central axis of the reactor where turbulence is low. It is also possible to construct a reactor according to this invention in which only one sparger is employed.

Returning to FIG. 1, a second reactant inlet 2b is used to introduce another reactant into the reactor. This other reactant may be comprised of a different substance than was introduced through reactant inlet 2 or it may be the same. The second reactant inlet 2b is also formed of piping, conduit, tubing or other hollow vessel used to transport gases or vapors. A jet 5 is affixed to the end of this second reactant inlet. This jet 5 is fashioned so that a second reactant enters the reactor as a stream and is not substantially diffused until it enters the proximity of the well mixed reaction zone 6. The term jet as used throughout this specification refers to a fitting on the reactor inlet which allows the reactant to be directed towards the reaction zone. In its broadest sense, a jet may be comprised of the opening of the reactant inlet 2b directed towards the reaction zone. However, preferred embodiments incorporate machined nozzles. More than one second reactant inlet and jet may be used in a reactor. Indeed, numerous jets and inlets can be used.

A well mixed reaction zone 6 is created in the area substantially between the spargers 3. This area is defined in part by the nature of the injection of the reactants. That is, the distance between the spargers and the volume of the reactants that the zone is designed to handle are determined according to the kinetics of the reaction so that molecular collisions occur rapidly.

The preparation of allyl chloride from propylene and chlorine in a preferred embodiment of the invention provides an example of how the reactor operates and how the reaction zones are defined. The reactor is cylindrical and has a length about three times its diameter. A first reactant inlet 2 is placed so that the nozzles 4 in a first sparger 3 are positioned to allow reactant to enter the reaction zone just ahead of the plane of the sparger. This can be relatively close to one end of the reactor 9. Chlorine gas is introduced into the reactant inlets 2 and sparged into the reactor. Another first reactant inlet 2 is placed so that the nozzles of its attached sparger 3 are directed at the nozzles of the other sparger and are close enough so that a reactant ejected from a sparger reaches the opposing sparger without substantial diminution of energy. The spargers are arranged so that an arm of one bisects the distance between two arms of the opposing sparger. Staggering the opposing sparger arms, while not critical, is preferred so that the interaction between the nozzles is minimized.

A second reactant inlet 2b is placed so that its attached jet 5 lies immediately behind the first sparger 3. The jet is best positioned when it is tangential with respect to the wall of the reactor. However, the jet may also be canted to conform with other design parameter thereby rendering it position with respect to the reactor wall substantially tangential. The outlet 8 is positioned at the end 10. A well mixed reaction zone 6 is comprised of the area substantially between the spargers and a plug flow reaction zone 7 is comprised of the area substantially between the second sparger and the outlet. A laminar flow reaction zone can be used in place of a plug flow reaction zone.

For a reactor with total volume of 250 to 300 cc, about 1.3 to 1.5 lbs/hr of chlorine are injected into the first reactant inlets at a pressure of about 20 to 70 psig and about 80° to 200° F. It has been found that the distribution of the chlorine between the first reactant inlets can affect the selectivity of the reaction. Where two opposing spargers are used to introduce chlorine, the distribution should be at least 50:50 as between the upstream and downstream sparger. However, improved results are obtained by biasing the introduction of chlorine towards the upstream sparger. This improvement in selectivity can continue until the distribution of reactant introduction is 80:20, upstream to downstream sparger. The term "upstream sparger" refers to the sparger in closest proximity to the second reactant inlet/jet while "downstream sparger" refers to the sparger opposite to the upstream sparger and closer to the outlet of the reactor.

As chlorine enters the first reactant inlet, about 2 to about 6 lbs per hour of propylene are injected into the second reactant inlet (and out the jets) at about 15 to about 50 psig and about 300° to about 700° F. The reactants are not premixed. Preferably, reaction temperature in the well mixed reaction zone is between about 850° F. and about 900° F. These temperatures and pressures are selected to provide the mixture with the energy needed to make reactants mix rapidly and to minimize the production of byproducts (here 1,2-dichloropropane). Injection of this first reactant, here chlorine, occurs under conditions necessary to cause entering reactant molecules to collide substantially instantaneously.

As noted above, positioning of the various means for introducing reactants and the manner in which the reactants are charged contributes to the selectivity and rapidity of the reaction taking place in the reactor. Without being bound to theory, it is believed that these factors create a mixing of reactants at a preferred energy state. This energy is imparted to the system by virtue of the speed and distribution of the entry of reactants through the spargers and the angular momentum of the reactant introduced through the jet. This relationship can be defined by the ratio of the velocity of reactant leaving the jet to the ratio of average velocity of the reacting mixture in the reactor. In more general terms, this is the ratio of the angular velocity provided by one of the reactants to the average axial velocity of the reacting mixture throughout the reactor. This ratio is referred to herein as the swirl number. It has been found that swirl numbers ranging from about 3 to 83 impart sufficient energy to practice this invention. It is preferred that the invention be practiced in a range from about 30 to 40.

Again, without being bound by theory, by positioning the reaction zone introduction means as described herein, most of the energy needed to drive the reaction is supplied by the reactants entering through those means. This can be a function of positioning of the spargers, for example, and the velocity of the reactants introduced through them. Further, the appropriate velocity can be attained through regulation of the pressure of the entering reactant. This means that it is not necessary to introduce reactants through the second reactant inlet 2b with a great deal of energy when the reactants entering the second reactant inlet do so with an angular momentum imparted to them so that their contact with reactants in the reaction zone results in three dimensional mixing. Thus, the positioning of the reactant introduction means, the positioning of the jets, and the pressure and temperature of the reactant can be used to describe the energy requirements for this reactor.

Distances between spargers may be adjusted depending upon the quantity of reactant flowing through the sparger and velocity with which it is imparted. That is, the distance between spargers is set at a point in which, given the velocity and volume of the reactant, one can expect a most rapid contact of the reactants entering the reaction zone. These distances are set so that the area between the spargers comprises between 20% and 50% of the volume of the reaction vessel.

To further facilitate achieving desired energy levels, nozzles 4 are affixed to holes bored along the front surface of the sparging arm 3b. It is preferred that each sparger have between six and ten sparging arms 3b. The sparging arms radiate outward from each reactant inlet 2. This configuration is referred to as a "spider" configuration of sparging arms. Increasing the number of nozzles about the circumference of the reaction zone increases the efficiency of the reaction. It is even more preferred to have all nozzles at least a half of a reactor radius away from the central axis of the reactor. However, the nozzles should not be placed so close to the wall of the reactor that special metallurgy would be required. Thus, if it is desirable to have a large number of nozzles, the use of a ring arrangement as opposed to the spider configuration shown in FIG. 2 and 3 is desired. Some embodiments of this invention may incorporate numerous nozzles on each sparging arm. In such a case, it is preferred that the nozzle closest to the central axis of the reactor be located at least half of a reactor radius away from the axis. Unless appropriate metallurgy is used (such as nickel plating), it is also preferred that the nozzle closest to the reactor wall (inner surface) be located at least one third of a reactor radius away from the reactor wall.

Figure 4:
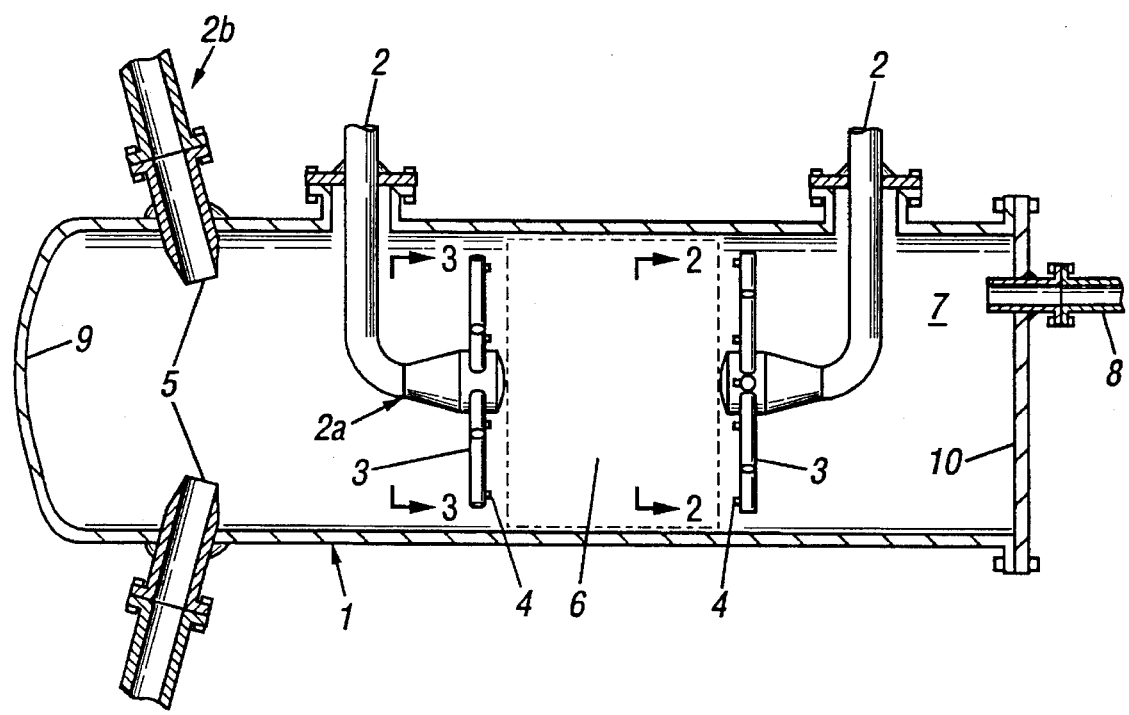
FIG. 4 is a side cutaway view of an embodiment of the instant invention.
Figure 5:
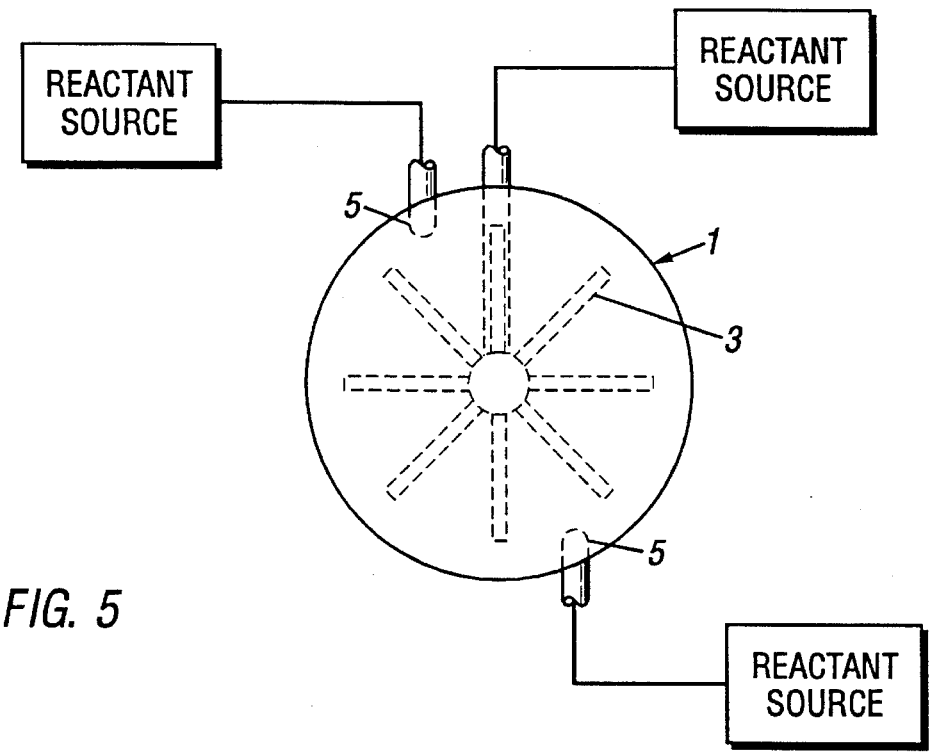
FIG. 5 is a rear partial cutaway view of the embodiment of FIG. 4.

In an embodiment of the invention in which allyl chloride is produced from propylene and chlorine, propylene is introduced into the reactor through the reactor inlet 2b and is further directed by jet 5 in a relatively coherent stream to the proximity of the spargers 3. For a reactor pressure of about 15 to 20 psig, propylene is introduced at temperatures between about 400° F. and about 700° F. The propulsion of the propylene imparts an angular momentum to the chlorine stream it contacts and creates a three dimensional flow in the well mixed reaction zone 6. It is preferred that this flow be substantially cyclonic but that the angular velocity not be so large as to cause a significant recirculation bubble around the central axis of the reactor. By substantially cyclonic it is meant that the predominant flow of the reactants inside the well mixed reaction zone in which mixing occurs radially and axially. Such mixing patterns can be semispherical, spherical, heliculoid, or a combination thereof. However, it will be understood that not all reactant will exhibit such behavior. A small amount of noncyclonic flow may occur at the central axis and at the fringes of the well mixed reaction zone, for example. FIGS. 4 and 5 illustrate an embodiment of this invention having two jets. FIG. 4 shows two jets 5 and their positioning relative to the central axis of the reactor. The jets are placed behind one of the spargers. They are directed so that the flow of reactants is toward the well mixed reaction zone and so that the streams of reactant cross paths. That is, if one were to draw a line starting at each jet and terminating at the vessel wall, the two lines would be complementary about the central axis of the reactor. These jets can be oriented so that each forms an angle from greater than 0 to less than 90° relative to a longitudinal plane running through the reactor. It is preferred that the jets be positioned so that the flow of reactants is tangential to the central axis of the well mixed reaction zone.

FIG. 5 illustrates the embodiment of FIG. 4 with further illustration of the relationship of the jets. This figure shows that the jets are positioned so that the reactants leaving one jet do not collide, mix, or interfere with the reactants of the other. This is accomplished by placing the jets in different transverse planes. Thus, when two jets are employed they are positioned as described above and are placed along any different transverse plane which will not result in interference among the reactants. If necessary, more than one second reactant inlet 2b can be used. This may be necessary to add a greater volume of reactant or to provide greater angular momentum to the well mixed reaction zone 6.

The three dimensional cyclonic character that is induced in the well mixed reaction zone is predominantly a macromixing phenomena. One aspect of the induced three dimensional cyclonic character is to ensure that a homogeneous mixture is rapidly achieved through reactant flow, recycling, and recirculation of reactant current. This also facilitates micromixing. This combination of improved micromixing and macromixing avoids anomalous hot spots and anomalous reaction rates within different parts of the reaction zones. The reduction in hot spots and the combination of improved micromixing and macromixing in general further reduces coke formation and thus improves product yield while reducing reactor maintenance requirements.

Mixing of the reactants is rapid, direct, and occurs throughout the area shared by propylene and chlorine. It is this area which comprises the well mixed reaction zone. Molecular collisions occur in three dimensions in this well mixed reaction zone. In reactions where high temperatures are favorable to drive a particular reaction mechanism, this well mixed reaction zone has a homogeneous high temperature profile. Multiple injections of reactants enhance this homogeneous profile through the character of mixing that is attained.

The well mixed reaction zone 6 is of such a dimension that the cyclonic mixing occurs substantially instantaneously therein. In the reaction of propylene and chlorine to produce allyl chloride, this reaction time is between about 500 and 800 milliseconds. This does not necessarily mean, however, that the reaction will come to completion in that zone. In most exothermic reactions, a hot spot will be formed somewhere in the well mixed reaction zone 6. If the hot spot is too hot, coke formation and isomerization can become problematic depending upon the kinetics of the reaction. Of course, the well mixed reaction zone of the instant invention has a relatively homogenous high temperature profile. Nevertheless, there will be one or more spots that are hotter than the rest of the reaction zone. Allowing the reactants to make rapid contact while avoiding the potential detrimental effects of lengthy exposure to a hot spot can be facilitated by moving the contacted reactants to another reaction zone within the reactor.

In a most preferred embodiment of the invention, the reactor comprises a plug flow reaction zone 7 in addition to the well mixed reaction zone 6. Thus, the flow of contacted reactants moves this mixture of products and unreacted reactants to the plug flow reaction zone 7 where this mixture is given additional residence time to complete the reaction. Since this mixture of products and unreacted reactants is out of the proximity of the well mixed reaction zone, it is no longer exposed to the hot spot and possible back mixing therein. It will be understood that the reaction is substantially completed within the well mixed reaction zone 6 and that the mixture flowing into the plug flow reaction zone 7 is comprised mostly of products. Thus, residence time finishes a small portion of the reaction. The combination of the near completion of reaction together with finishing the reaction in the absence of a hot spot ensures that isomerization is minimized, selectivity is high, and yield is high. The flow from the well mixed reaction zone to the plug flow reaction zone allows product to be easily withdrawn through the product outlet 8 where it can be captured or sent to other processes.

When propylene is reacted with chlorine to produce allyl chloride according to this invention, an exit temperature of about 910°–930° F. is attained at the product outlet. This is about 20° F. to 40° F. lower than the exit temperatures in prior art reactors. The reaction is substantially complete in between about 500 and 700 msec as compared to about 800 to 1000 msec using prior art methods. Yields in excess of 85 M % (on the basis of propylene) have been attained using this new reactor at a propylene to chlorine molar ratio of 2.9. Yields in excess of 88% M (on the basis of propylene) have been attained using this new reactor at a propylene to chlorine molar ratio of 5.8. Yields in excess of 90% M (on the basis of propylene) can be achieved by incorporating more than one reactor and staging chlorine addition. Prior art reactors typically attain molar yields of about 81 to about 82% M (on the basis of propylene). Undesirable byproducts such as 1,2 dichloropropane (DCPo) are greatly reduced. In this configuration of the invention, DCPo yield is reduced from the prior art level of 4–5 M % (based upon molar amounts of propylene present) to 0.5–2 M % (based upon molar amounts of propylene present). There is no need to specially prepare the surface of the reactors as with nickel plating or the like.

The reactor described above can also be used for a great number of other reactions in which rapid collisions can be facilitated by the combination of enhanced micromixing and macromixing character. This is especially true where the reactants have a propensity for forming isomeric byproducts.

The following examples are provided to more fully illustrate the invention. Such examples are not to be construed, however, as limiting the scope of the invention.

EXAMPLES

In the following examples, a cylindrical reactor 6 inches in length and 2 inches in diameter was used. Chlorine was introduced through two spargets placed about 2.5 inches apart. This resulted in a well mixed reaction zone (region) comprising about 40 to 50% of the reactor volume. The spargers had eight arms per sparger with each arm having one nozzle with an inner diameter of about 0.006 inches. Nozzles and sparget arms were positioned so that the nozzles were mid-way between the central axis of the reactor and the wall of the reaction vessel. Reactor configuration was as shown in FIG. 4 except that a pair of tangential jets was used to introduce propylene into the reactor. The reactor was operated at 15 psig. CP grade propylene and HP grade chlorine were obtained from Matheson Gas Products.

In each example, the reaction to produce allyl chloride was complete in from 500 to 700 msec. The gaseous effluent was analyzed via gas chromatography with flame ionization detector.

Example 1

About 1.4 lbs per hour of chlorine were injected into the reactor through the pair of spargers. The chlorine was introduced at a temperature of about 120° F. and a pressure of about 36 psig. The chlorine injection was split about equally between the two spargers. That is, about 50% of the total volume of chlorine was introduced through each sparger.

About 2.4 lbs/hour of propylene were injected at a temperature of about 490° F., and a pressure of about 18 psig.

The temperature in the well mixed reaction zone was between 850° F. and 900° F., and the temperature at the reactor exit was about 910° F. The wall temperature was between 850° F. and 883° F.

The reaction resulted in product having selectivity on a propylene molar basis of 85.6% allyl chloride, 0.5% 1,2-dichloropropane, 7.4% 1,3-dichloropropene, and 2.7% 2-chloropropene.

This example illustrates the high selectivity and yield achieved through the use of a reactor according to this invention.

Example 2

About 1.4 lbs per hour of chlorine were injected into the reactor at a temperature of about 120° F. and a pressure of about 40 psig in the upstream sparger and 33 psig in the downstream sparger. About 65% of the total volume of chlorine was injected through the upstream sparger with the balance injected through the downstream sparger.

About 2.4 lbs/hour of propylene were injected through the pair of tangential jets at a temperature of about 490° F. and a pressure of about 18 psig.

The temperature in the well mixed reaction zone was between 850° F. and 900° F. and the temperature at the reactor exit was about 907° F. The wall temperature was between 850° F. and 885° F.

The selectivity on a propylene molar basis was 85.5% allyl chloride, 0.5% 1,2-dichloropropane, 7.3% 1,3-dichloropropene, and 2.8% 2-chloropropene.

Example 3

About 1.4 lbs per hour of chlorine were injected into the reactor at a temperature of about 120° F. and a pressure of about 50 psig in the upstream sparger and 19 psig in the downstream sparger. About 80% of the total volume of chlorine was injected through the upstream sparger with the balance injected through the downstream sparger. About 2.4 lbs/hour of propylene were injected through the pair of tangential jets at a temperature of about 490° F. and a pressure of about 18 psig.

The temperature in the well mixed reaction zone was between 850° F. and 890° F. and the temperature at the reactor exit was about 906° F. The wall temperature was between 850° F. and 882° F.

The selectivity on a propylene molar basis was 84.9% allyl chloride, 0.8% 1,2 dichloropropane, 8.0% 1,3-dichloropropene, and 2.7% 2-chloropropene.

Example 4

About 1.4 lbs per hour of chlorine were injected into the reactor through the pair of 8 armed spargers at a temperature of about 120° F. and a pressure of about 33 psig. Chlorine introduction was split about equally between the two spargers. About 4.8 lbs/hour of propylene was injected through a pair of tangential jets, at a temperature of about 680° F., and a pressure of about 31 psig.

The temperature in the well mixed reaction zone was between 850° F. and 900° F. The temperature just downstream of the downstream nozzle was about 929° F. and the temperature at the reactor exit was about 897° F. The wall temperature was between 850° F. and 883° F.

The selectivity on a propylene molar basis was 87.7% allyl chloride, 0.9% 1,2-dichloropropane, 2.4% 1,3-dichloropropene, and 3.6% 2-chloropropene.

Example 5

About 1.4 lbs per hour of chlorine were injected into the reactor described in Example 1 at a temperature of about 120° F., and a pressure of about 40 psig in the upstream sparger and 33 psig in the downstream sparger. About 65% of the total volume of chlorine was injected through the upstream sparger with the balance injected through the downstream sparger. About 4.8 lbs/hour of propylene were injected through the pair of tangential jets at a temperature of about 700° F. and a pressure of about 31 psig.

The temperature in the well mixed reaction zone was between 840° F. and 900° F. and the temperature at the reactor exit was about 901° F. The wall temperature was between 850° F. and 885° F.

The selectivity on a propylene molar basis was 88.3% allyl chloride, about 0.5& 1,2-dichloropropane, 4.1% 1,3-dichloropropene, and 3.7% 2-chloropropene.

This example illustrates that biasing chlorine introduction through an upstream reaction zone introduction means can result in an improvement in product selectivity and a decrease in the production of byproducts which are difficult to separate (most notably 1,2-dichloropropane).

Example 6

About 1.4 lbs per hour of chlorine were injected into the reactor at a temperature of about 120° F. and a pressure of about 50 psig in the upstream sparger and 19 psig in the downstream sparger. About 80% of the total volume of chlorine was injected through the upstream sparger with the balance injected through the downstream sparger. About 4.8 lbs/hour of propylene were injected through a pair of tangential jets, at a temperature of about 680° F., and a pressure of about 18 psig.

The temperature in the well mixed reaction zone was between 840° F. and 880° F., and the temperature at the reactor exit was about 894° F. The wall temperature was between 850° F. and 894° F.

The selectivity on a propylene molar basis was 88.4% allyl chloride, 1.2% 1,2-dichloropropane, 3.7% 1,3-dichloropropene, and 3.7% 2-chloropropene.

This example illustrates the improved yield of product attained by biasing the introduction of reactant through the upstream reaction zone introduction means.

We claim as our invention:

1. A chemical reactor comprising:

a reaction vessel;

at least two reaction zone introduction means each of said means comprising a reactor inlet and sparger, said inlet being in communication with a first source of reactant at one of said ends and the sparger being in communication with the interior of said reaction vessel, said spargers having a plurality of sparger arms radiating outward from the central axis of said inlet such that the sparger arms of one sparger are in opposition to those of another sparger and substantially bisect the distance between the sparger arms of said opposing sparger;

at least one injection jet in communication with a second source of reactant, said injection jet housed within said reaction vessel; at least one reactant of a chemical reaction being introduced into said reactor through said reaction zone introduction means, at least one reactant being introduced into said reactor through said injection jet, said injection jet positioned so that introduction of said reactants imparts a substantially three dimensional flow of said reactants;

a well mixed reaction zone comprising the area substantially between said spargers within said reaction vessel wherein said reactants are mixed;

and an outlet having two ends, one end being in communication with the interior of the reaction vessel and one end being in communication with the exterior of the reaction vessel.

2. The reactor of claim 1 further comprising a flow region substantially adjacent to said well mixed reaction zone.

3. The reactor of claim 1 comprising two reactor inlets.

4. The reactor of claim 1 wherein said sparger further comprises a nozzle through which reactant is injected into said reactor.

5. The reactor of claim 4 wherein the introduction of said reactant through said injection jet imparts a three dimensional cyclonic character to said reactants in said well mixed reaction zone.

6. The reactor of claim 1 wherein said injection jet is positioned so that introduction of said reactant into said reactor occurs substantially tangential to the central axis of said reactor.

7. The reactor of claim 1 having a plurality of injection jets, each of said injection jets positioned at an angle greater than 0° and less than 900 with respect to a longitudinal plane of said reactor provided that said jets lie in different transverse planes.

8. The reactor of claim 7 having two injection jets.

9. The reactor of claim 8 wherein said jets are positioned so that said reactant introduced through one of said jets occurs at an angle supplementary to the introduction of said reactant by the other jet.

10. The reactor of claim 1 wherein the angle of each of said jets with respect to the central axis of said reactor is equal.

11. The reactor of claim 1 wherein each of said spargers comprise a ring about the central axis of said reactor.

12. The reactor of claim 1 having a swirl number between about 3 and 83.

13. The reactor of claim 12 having a swirl number between about 30 and 40.

14. The reactor of claim 1 wherein each of said injection jet is positioned at an angle greater than 0° and less than 90° with respect to a longitudinal plane of said reactor.

15. A chemical reactor comprising:

a substantially cylindrical reaction vessel;

at least two reactant inlets protruding into said reaction vessel, each of said inlets having at least two ends, said inlets being in communication with a chlorine source at one of said ends and the interior of said reaction vessel at said other end;

at least two spargers, at least one sparger affixed to each of said reactant inlets at said end in communication with the interior of said reaction vessel; said spargers being substantially opposed to each other;

a plurality of sparger arms radiating outward from a point on the central axis of said reactant inlet, said sparger arms comprising said sparger; each of said sparger arms substantially bisecting the distance between two opposing sparger arms;

at least one nozzle affixed to each of said sparger arms;

at least two injection jets housed within said reaction vessel at an angle substantially tangential to the central axis of said reaction vessel;

a well mixed region; said well mixed region comprising an area substantially between said spargers;

a plug flow region comprising an area substantially adjacent to said well mixed region; and an outlet adjacent to said plug flow region said outlet being in communication with the exterior of said reactor.

* * * * *